United States Patent [19]

Rouy et al.

[11] 4,367,180
[45] Jan. 4, 1983

[54] PROCESS FOR THE PREPARATION OF MALATHION

[75] Inventors: Noël Rouy, Yerres; Georges Gros, Bourg la Reine, both of France

[73] Assignee: Rhone-Poulenc Agrochimie, Lyons, France

[21] Appl. No.: 242,539

[22] Filed: Mar. 11, 1981

[30] Foreign Application Priority Data

Mar. 21, 1980 [FR] France ............................... 80 07243

[51] Int. Cl.$^3$ ............................................. C07F 9/165
[52] U.S. Cl. ..................................... 260/978; 260/990
[58] Field of Search ....................... 260/978, 942, 990

[56] References Cited

U.S. PATENT DOCUMENTS 3,463,841  8/1969  Backlund et al. .................. 260/978

Primary Examiner—Anton H. Sutto
Attorney, Agent, or Firm—Burns, Doane, Swecker & Mathis

[57] ABSTRACT

Process for the preparation of malathion by reacting O,O-dimethyl-dithiophosphoric acid with ethyl maleate in the presence of a solvent which forms a heterogeneous azeotrope with the O,O-dimethyl-dithiophosphoric acid.

18 Claims, No Drawings

PROCESS FOR THE PREPARATION OF MALATHION

The present invention relates to an improved process for the preparation of insecticides and more particularly of malathion.

Malathion, which is also called S-[1,2-(dicarbethoxy)-ethyl]O,O-dimethyl phosphorodithioate, is a product of the formula

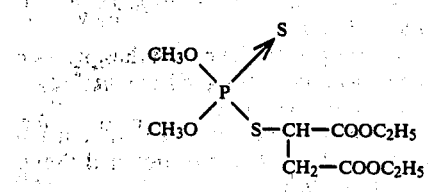

Various processes for the preparation and/or purification of malathion are known and have led to more or less satisfactory results, using reactants of diverse types as the starting materials. French Pat. No. 1,541,883 describes a process for the preparation of malathion by reacting O,O-dimethyl-dithiophosphoric acid with ethyl maleate in a solvent medium, in which process the reaction mixture is subjected to evaporation in an evaporator with a short passage time (also referred to as flash distillation).

O,O-Dimethyl-dithiophosphoric acid has the formula

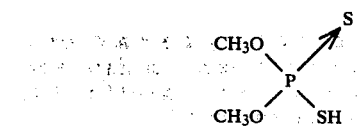

Although the process of French Pat. No. 1,541,883 constitutes an advance compared with the earlier processes, this process exhibits several disadvantages which are desirable to overcome.

In particular, the productivity of the equipment is greatly reduced by the presence of a large amount of solvent at the start of the reaction, by the resulting limitation of the reaction rate and by the limitation imposed on the degree of conversion of the reactants.

These disadvantages are only partially overcome by continuous rapid evaporation of the whole reaction mixture; indeed, this evaporation is made more difficult by the very fact that the mixture to be distilled is a complex mixture, and that the evaporation is carried out on fairly large amounts of products.

Moreover, the recycling of the unconverted ethyl maleate from one operation to the next exhibits the disadvantage of increasing the proportion of ethyl fumarate (isomerization product of the maleate), which reacts more slowly and accumulates in the reaction medium; its removal requires special treatments, e.g. with sulfides or sulfites.

One object of the present invention is to provide a process which makes it possible to produce highgrade malathion.

Another object of the present invention is to provide a process which makes it possible to produce malathion with a good productivity and good yields.

It has now been found that these objects can be achieved by virtue of the process according to the invention.

This process comprises (a) reacting ethyl maleate with an excess of O,O-dimethyldithiophosphoric acid in the presence of a solvent which is capable of forming an azeotrope with the O,O-dimethyldithiophosphoric acid, (b) distilling an azeotropic mixture of O,O-dimethyl-dithiophosphoric acid and the solvent, (c) cooling this distillate and separating it by decantation, (d) recycling the phase (of this cooled and separated distillate) comprising mainly the solvent and a small amount of O,O-dimethyl-dithiophosphoric acid into the reaction medium comprising mainly the ethyl maleate and the O,O-dimethyl-dithiophosphoric acid (and the malathion in the process of being formed), and (e) drawing off the phase (of the cooled and separated distillate) comprising mainly the O,O-dimethyl-dithiophosphoric acid and a small amount of solvent.

The solvent which is capable of forming an azeotrope with the O,O-dimethyl-dithiophosphoric acid is in fact a solvent which is capable of forming a heterogeneous liquid mixture, at ambient temperature, with the O,O-dimethyl-dithiophosphoric acid, i.e. the mixture of the two constituents is capable of being separated by decantation. Amongst the solvents of this type, those having a b.p. of between 160° and 240° C. are advantageously used. The used solvent may be a simple solvent or a mixture of several solvents.

More specifically, saturated hydrocarbons having a b.p. of between 160° and 240° C., and more especially aliphatic hydrocarbons, such as decane, dodecane and tetradecane, and cycloaliphatic hydrocarbons, such as decalin, are preferably used as the solvent.

The excess of O,O-dimethyl-dithiophosphoric acid, relative to the ethyl maleate, is such that the molar ratio of the amounts of these two reactants employed is between 1.05 and 2, preferably between 1.15 and 1.6.

The use of this excess of acid makes it possible to obtain good yields relative to the ethyl maleate, which has the additional advantage of contributing towards a decrease in the proportion of residual ethyl maleate in the final malathion, this being a significant advantage.

The reaction of the O,O-dimethyl-dithiophosphoric acid with the ethyl maleate is carried out by simply bringing the reactants into contact; the mixture usually starts to warm up by itself, and the reaction is therefore left to start by itself; the reaction can then be continued by external heating to a temperature between 50° and 100° C., preferably between 60° and 90° C.

In the process according to the invention, the degree of conversion of the ethyl maleate is generally greater than 90%, preferably greater than 99%.

The amount of solvent, and in particular of saturated hydrocarbon, present in the reaction medium is generally between 1 and 15% by weight, relative to the O,O-dimethyl-dithiophosphoric acid employed, preferably between 3 and 8%.

The mixture of O,O-dimethyl-dithiophosphoric acid and solvent (saturated hydrocarbon) is advantageously in the form obtained by the known processes for the preparation of O,O-dimethyl-dithiophosphoric acid, carried out in the presence of the said solvent.

The azeotropic distillation (b) is advantageously carried out only at the end of the reaction, for the purpose of maintaining an excess of O,O-dimethyl-dithiophosphoric acid. It is preferably carried out under an absolute reduced pressure of less than 80 millibars and more especially of less than 27 millibars.

The azeotropic distillate is cooled (c) to the temperature at which the mixture of O,O-dimethyldithiophosphoric acid and solvent (saturated hydrocarbon) dissociates into two liquid phases. This cooling temperature is advantageously between 0° and 50° C., preferably between 15° and 40° C.

In the separation (c) of the mixture of O,O-dimethyl-dithiophosphoric acid and solvent by decantation, the upper phase is generally the phase containing an excess of solvent; in other words, this upper phase is the liquid phase containing mainly the solvent and a small amount of O,O-dimethyl-dithiophosphoric acid.

In the same separation (c) of the mixture of O,O-dimethyl-dithiophosphoric acid and solvent by decantation, the lower liquid phase is generally the phase containing an excess of O,O-dimethyl-dithiophosphoric acid; in other words, this lower phase is the phase comprising mainly the O,O-dimethyl-dithiophosphoric acid and a small amount of solvent.

The lower phase is drawn off (e) and can be reused for a subsequent operation.

The upper phase is advantageously recycled (d) into the reaction mixture containing the malathion; even if the reaction has ended at the time when this recycling takes place; this recycling makes it possible to introduce the solvent (saturated hydrocarbon) into the reaction mixture, and this enables the azeotropic distillation to be continued even though the overall amount of solvent (saturated hydrocarbon) employed is small. This recycling also enables the azeotropic distillation of the O,O-dimethyl-dithiophosphoric acid to be continued at a temperature which minimizes the degradation of this acid.

When these various operations have been completed, the reaction mixture contains mainly malathion and also a small amount of O,O-dimethyl-dithiophosphoric acid, of solvent (saturated hydrocarbon) and, if appropriate, of other impurities.

If it is desired to obtain an improved grade of malathion, it is possible to remove the O,O-dimethyl-dithiophosphoric acid and other acid impurities by neutralization with an alkaline agent and washing with water; the O,O-dimethyl-dithiophosphoric acid is then removed in the form of an aqueous solution of its alkali metal salt, this aqueous solution being immiscible with the malathion.

If it is desired to improve the purity of the malathion even further, it can be subjected to additional treatments.

Rapid evaporation (or flash distillation) of the volatile fractions may be mentioned as the preferred additional treatment. Rapid evaporation has the advantage of avoiding any inopportune decomposition of the products present, and in particular of the malathion.

This distillation or rapid evaporation is advantageously carried out continuously, the residence time of the products treated being less than 5 minutes, preferably less than 1 minute. Thin film evaporators are particularly suitable for this kind of operation.

According to an advantageous variant of the invention, rapid evaporation in the presence of water (or with steam distillation), and, if appropriate, rapid evaporation under reduced pressure, are carried out.

Rapid evaporation in the presence of water is carried out at a temperature which is most frequently between 90° and 150° C. and preferably between 100° and 120° C.; the presence of water makes it possible to facilitate the removal of the residues of solvent (saturated hydrocarbon) and of ethyl maleate and fumarate, in particular by the formation of an azeotrope (or azeotropes). The water makes it possible to carry out steam distillation. An amount of water of between 20 and 80% by weight, relative to the malathion, is advantageous.

Rapid evaporation under reduced pressure is advantageously carried out at between 70° and 150° C., at absolute pressures of between 1 and 65 millibars, preferably between 4 and 20 millibars.

The process according to the invention thus makes it possible to obtain malathion with a good productivity, a good yield and a high degree of purity.

The following example, which is given without implying a limitation, illustrates the invention and shows how it can be put into effect.

EXAMPLE

Crude, O,O-dimethyl-dithiophosphoric acid (240.8 g), containing 6% by weight of dodecane, is introduced into a 1 liter reactor and ethyl maleate (172 g) is then added gradually in the course of 1 hour 30 minutes.

This mixture is then kept at a temperature of 90° C. for 4 hours. Distillation is then carried out under a reduced absolute pressure of about 7 to 13 millibars; the azeotropic mixture of dodecane+O,O-dimethyl-dithiophosphoric acid is distilled in the form of vapor, and the distillate is cooled to 25° C. and separated into two layers by decantation; the upper layer, containing mainly dodecane, is reintroduced continuously into the reactor.

The reaction medium containing the malathion is neutralized with an aqueous solution of sodium bicarbonate. Malathion is thus obtained with a yield of 98%, relative to the ethyl maleate employed.

The malathion is purified by flash distillation (in a thin film evaporator) at a temperature of 110° C. and in the presence of 50% (by weight) of water; a second flash distillation (in a thin film evaporator) is then carried out at 105° C. and under a reduced absolute pressure of 6.6 millibars (residence time <1 minute).

95% pure malathion (328 g) is thus obtained.

The amount of O,O-dimethyl-dithiophosphoric acid recovered in the first distillation represents 76% of the excess employed in the reaction and is used for a further operation identical to the one already described.

We claim:

1. A process for the preparation of malathion, which comprises:
   (a) reacting ethyl maleate with an excess of O,O-dimethyldithiophosphoric acid in the presence of a solvent which forms an azeotrope with the O,O-dimethyldithiophosphoric acid at elevated temperatures and a heterogeneous liquid mixture at ambient temperature,
   (b) distilling off an azeotropic mixture of O,O-dimethyldithiophosphoric acid and the solvent upon completion of the reacting (a),
   (c) cooling collected distillate sufficiently to thereby allow same to dissociate into phases comprising a solvent rich phase and an acid rich phase, and then separating the phase by decantation, then
   (d) recycling the solvent rich phase comprising mainly the solvent and a small amount of O,O-dimethyldithiophosphoric acid to the reaction medium, and (e) drawing off the acid rich phase comprising mainly the O,O-dimethyldithiophosphoric acid and a small amount of solvent.

2. A process according to claim 1, wherein the solvent is a saturated hydrocarbon having a b.p. of between 160° and 240° C.

3. A process according to claim 2, wherein the solvent is decane, dodecane, tetradecane or decalin.

4. A process according to claim 3, wherein the solvent is dodecane.

5. A process according to one of claim 1, 2, 3 or 4, wherein the O,O-dimethyl-dithiophosphoric acid drawn off in step (e) is used in step (a) of a further operation.

6. A process according to one of claim 1 or 2, wherein the amount of the solvent which is capable of forming an azeotrope is between 1 and 15%, relative to the O,O-dimethyl-dithiophosphoric acid employed.

7. A process according to claim 6, wherein the amount of solvent is between 3 and 8% of the acid employed.

8. A process according to one of claim 1 or 2, wherein the molar ratio of O,O-dimethyl-dithiophosphoric acid to the ethyl maleate is between 1.05 and 2.

9. A process according to claim 8, wherein the molar ratio acid/maleate is between 1.15 and 1.6.

10. A process according to one of claim 1 or 2, wherein the reaction temperature is between 50° and 100° C.

11. A process according to one of claim 1 or 2, wherein, in step (c), the distillate is cooled to between 0° and 50° C.

12. A process according to claim 11, wherein the cooling temperature is between 15° and 40° C.

13. A process according to one of claim 1 or 2, wherein, at the end of the reaction, the reaction medium is neutralized and washed with water, and the resulting malathion is subjected to rapid evaporation of the volatile fractions, the residence time in the evaporator being less than 5 minutes.

14. A process according to claim 13, wherein the residence time is less than 1 minute.

15. A process according to one of claim 13, which comprises carrying out rapid evaporation with steam distillation, and rapid evaporation under reduced pressure.

16. The process according to claim 1 or 2, wherein the amount of solvent employed is between 1 and 15% of the O,O-dimethyldithiophosphoric acid employed and the molar ratio of acid/ethyl maleate is between 1.05 and 2.

17. The process according to claim 16, wherein the reaction temperature is between 50° and 100° C. and the distillate in step (c) is cooled to between 0° and 50° C.

18. The process according to claim 16, wherein the reaction medium is neutralized and washed with water at the end of the reaction and the resulting malathion is subjected to rapid evaporation of volatile fractions, with the residence time in an evaporator being less than 5 minutes.

* * * * *